United States Patent [19]

Sturtz et al.

[11] Patent Number: 4,464,346

[45] Date of Patent: Aug. 7, 1984

[54] EXTRACTION OF URANIUM WITH TRIPHOSPHONIC ESTERS

[75] Inventors: Georges Sturtz, Brest; Thierry Pensec, Bannalec; Jean-Claude Gautier, Billere, all of France

[73] Assignee: Societe Nationale Elf Aquitaine (Production), France

[21] Appl. No.: 166,291

[22] Filed: Jul. 7, 1980

[30] Foreign Application Priority Data

Jul. 9, 1979 [FR] France .................... 79 17737

[51] Int. Cl.$^3$ ............................................. C01G 43/00
[52] U.S. Cl. ...................................... 423/10; 260/932
[58] Field of Search ...................... 423/8, 10; 210/634; 260/932; 252/184

[56] References Cited

U.S. PATENT DOCUMENTS

| | | | |
|---|---|---|---|
| 2,765,279 | 10/1956 | Nüsslein | 260/932 |
| 3,256,370 | 6/1966 | Fitch et al. | 260/932 |
| 3,471,552 | 10/1969 | Budnick | 260/932 |
| 3,534,125 | 10/1970 | Knollmueller | 260/932 |
| 3,743,688 | 7/1973 | Nicholson et al. | 260/932 |
| 3,993,728 | 11/1976 | Schulz | 423/10 |
| 4,105,741 | 8/1978 | Wiewiorowski et al. | 423/10 |

FOREIGN PATENT DOCUMENTS 410029 4/1972 U.S.S.R. .................... 260/932

OTHER PUBLICATIONS

Hurst, "Solvent Extraction of Uranium from Wet Process Phosphoric Acid", ORNL-TM-2522, p. 39, (1969).

*Primary Examiner*—Edward A. Miller
*Attorney, Agent, or Firm*—Ostrolenk, Faber, Gerb & Soffen

[57] ABSTRACT

Triphosphonic esters, each of the three phosphorus atoms of which is bound to a carbon atom of the same hydrocarbon group, having 2 or 4 free acid functions or two salt functions, may be used for various known uses of phosphonates, including the extraction of heavy metals.

8 Claims, No Drawings

EXTRACTION OF URANIUM WITH TRIPHOSPHONIC ESTERS

This invention relates to a new type of phosphonic compound, and particularly to triphosphonic esters. It also comprises a process for the production of said compounds.

Various phosphonates and diphosphonates are known in industry, where they are used for various purposes. Thus, wetting agents, emulsifiers and plasticizers are known having a base of phosphonates, the organic group of which directly bound to the phosphorus is ketalic, acetalic or dihydroxy; such products, which can also be used to retard combustion of cellulose and different polymers, are described in French Pat. No. 1,459,049. Antioxidant phosphonates form the object of French Pat. No. 2,048,493 while the diphosphonates are proposed as antioxidants and stabilizers for polymers in accordance with French Pat. No. 2,268,800. Polymeric phosphonates and diphosphonates form part of various resin compositions in accordance with U.S. Pat. No. 3,220,989 and French Publication No. 2,184,706. Furthermore, an entire range of pesticides having a base of sulfur phosphonates are available on the market, in particular under the brand name "Demephon." Another interesting application of certain diphosphonates is the complexing of heavy metals; this use as chelating agent is indicated, for instance, in U.S. Pat. Nos. 2,599,807 and 2,609,390. It is to be noted that in the derivatives of diphosphonic acids used up to now, the bond between the two phosphorus atoms is effected via oxygen and/or sulfur, which is the cause for a certain lack of stability of the compounds in question. In view of the extremely general usefulness of these compounds, it was of interest to seek more stable phosphonates.

The work of the applicants has led to the preparation of new phosphonates, characterized by the fact that three phosphonic groups are attached to the hydrocarbon group A'. These new products have the advantage of chemical stability and are suitable for various general uses of the known phosphonates; they are suitable in particular as chelating agents for heavy metals and as agents for the extraction of certain metals. Thus, they are suitable for the extraction of nickel, uranium or other metals from the materials containing them.

The new triphosphonic esters in accordance with the invention can be represented by the formula

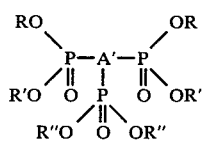

I in which A' is a trivalent hydrocarbon group which may, for instance, be aliphatic, cycloaliphatic, aryl or alkaryl; R is a hydrocarbon radical which is also aliphatic, cycloaliphatic, aryl or alkaryl and more particularly a $C_1$ to $C_{18}$ alkyl and particularly a lower alkyl, that is to say a $C_1$ to $C_4$ alkyl; R may possibly be a hydrogen atom; R' can be a hydrogen atom, a cation—in particular alkali, ammonium or quaternary ammonium—or else a hydrocarbon radical which is similar to or different from R; R" is also an aliphatic, cycloaliphatic, aryl or alkaryl hydrocarbon radical which may possibly be the same as or different from R and R'; in particular R" may advantageously be a $C_4$ to $C_{20}$ alkyl or preferably a $C_6$ to $C_{18}$ alkyl.

Although A' may contain any number of carbon atoms, interesting products have rather small A' groups, particularly $C_1$ to $C_6$ groups.

Thus, the triphosphonic ester in accordance with the invention may be a hexaester when R, R' and R" are hydrocarbon radicals; it is a tetraester diacid when R" is H, and a tetraester disalt if R' is a cation.

Depending on the nature of the groups A', R, R' and R", these products may be liquid or solid, which permits the selection of the triphosphonate suitable for each desired application. Thus, for instance, if A' is —$CH_2$—CH—$CH_2$—, R methyl, R' Na cation and R" n-butyl the product is liquid, while it is solid if R" is n-octyl.

In accordance with one special feature, each of the phosphorus atoms of the product of the invention is bound to a different carbon atom of the hydrocarbon group A'.

A process for the preparation in accordance with the invention of the above-defined compounds involves, first of all, reacting an alkali metal derivative of a phosphite diester (III) with a tetraester of diphosphonic acid (II) in which the two phosphorus atoms are bound by a hydrocarbon bridge containing a double bond. This reaction can be illustrated by the following example in which the bridge between the two phosphorus atoms of the starting product consists of the allyl group —CH=CH—$CH_2$— which contains an ethylene unsaturation:

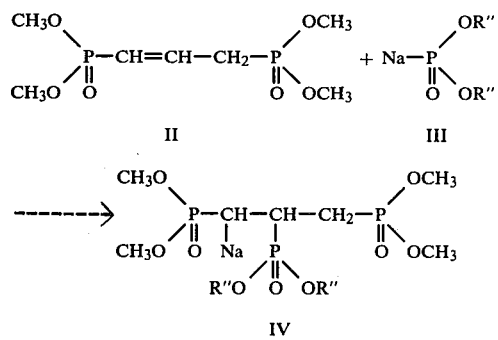

The derivative IV formed, the sodium salt of which can be written

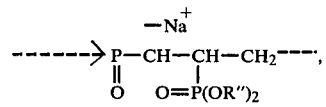

gives, upon acidification, the desired triphosphonate

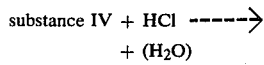

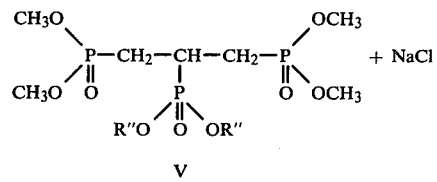

Of course, the starting compound (II) may instead of the —CH$_3$ have other radicals or hydroxyls and instead of the allyl bridge another reactive unsaturated group. Thus, triphosphonates can be prepared from the corresponding diphosphonates. From a practical standpoint, it should be noted that tetramethyl diphosphonate is the most accessible industrially.

Starting from the triphosphonate V, one can—in accordance with the invention—pass to a corresponding metallic di-salt by the action of a salt MX in which M is a metal atom and more particularly an alkali, or alkaline earth atom or Zn, or else an ammoniacal cation, that is to say NH$_4$ or amine, while X is the anion, in particular halogen, sulfate, sulfite, acetate or other.

This reaction, which takes place within an organic solvent in which the salt MX is less ionized than in water, can be written:

$$\text{substance V} + 2MX \longrightarrow$$

$$\begin{array}{c} \text{CH}_3\text{O} \phantom{XXXXXXXXXXXX} \text{OCH}_3 \\ \diagdown \phantom{XXXXXXXXXXXXXX} \diagup \\ \text{P—CH}_2\text{—CH—CH}_2\text{—P} \phantom{XX} + 2\text{CH}_3\text{X} \\ \diagup \parallel \phantom{XXX} | \phantom{XXXXX} \parallel \diagdown \\ \text{MO} \phantom{X} \text{O} \phantom{XXX} \text{P} \phantom{XXXXX} \text{O} \phantom{X} \text{OM} \\ \phantom{XXXX} \diagup \parallel \diagdown \\ \phantom{XXX} \text{R''O} \phantom{X} \text{O} \phantom{X} \text{OR''} \\ \phantom{XXXXXXXX} \text{VI} \end{array}$$

The case in which M is sodium is in practice the most common. The reaction takes place best between 50° and 100° C., preferably with reflux of the solvent, over the course of several hours.

The disalt VI obtained is the substance of formula I with metal cation M in place of R'. In order to pass to the corresponding diacid in which the Rs are H, it is sufficient to hydrolyze the disalt VI, which can be done by treatment with aqueous solution of an acid, for instance HCl or H$_2$SO$_4$. In order to obtain the diacid directly, one can carry out a controlled acid hydrolysis which attacks only the methoxy group. This hydrolysis is effected, for instance, by means of dilute HCl, H$_3$PO$_4$ or H$_2$SO$_4$, or else by the action of a tertiary amine, in particular trimethylamine.

By a more extensive acid hydrolysis, the tetraacid is obtained, that is to say the product in which R and R' are hydrogen atoms.

The following non-limitative examples will serve to illustrate the invention.

EXAMPLES 1 TO 8

Preparation of Triphosphonates
To a solution of 0.05 mol of sodium phosphite $$(R''O)_2 - \underset{\underset{O}{\parallel}}{P} - Na$$

in 50 ml of tetrahydrofuran (THF) there is added, drop by drop, 0.05 mol of diphosphonate $$(CH_3O)_2 - \underset{\underset{O}{\parallel}}{P} - A' - \underset{\underset{O}{\parallel}}{P}(OCH_3)_2,$$

agitating in an inert atmosphere. The temperature of the medium is 30°–40° C. during this addition. The solution assumes an orange-red color.

The reaction is completed by heating under reflux for 5 hours, whereupon the THF is evaporated and taken up in dilute HCl. As the filtration of the whitish precipitate formed is rather difficult, the triphosphonate thus obtained is extracted by chloroform.

This manner of operation is repeated with phosphites of different R'' and with trimethyl diphosphonates of different A'. The results of the NMR examination of the products obtained are given below for each of Examples 1 to 8.

$$(CH_3O)_2P-CH_2-CH-P-(OCH_3)_2 \quad (1)$$
$$\phantom{XX}a \phantom{X} \overset{\parallel}{O} \phantom{X} b \phantom{X} c \phantom{X} | \phantom{X} \overset{\parallel}{O} \phantom{X} a$$
$$\phantom{XXXXXXXXXX} CH_2$$
$$\phantom{XXXXXXXXX} d \phantom{X} |$$
$$\phantom{XXXXXXXX} P-(OCH_2C_3H_7)_2$$
$$\phantom{XXXXXX} \overset{\diagup}{O} \phantom{XXX} e \phantom{XXX} f$$

Ha + He 3.6——→4.2 ppm (multiplet)
Hc 2.0——→2.7 ppm (multiplet)
Hb + Hd + Hf 0.8——→1.8 (multiplet)

$$(CH_3O)_2P-CH_2-CH-P-(OCH_3)_2 \quad (2)$$
$$\phantom{XX}a \phantom{X} \overset{\parallel}{O} \phantom{X} b \phantom{X} | c \phantom{X} \overset{\parallel}{O} \phantom{X} a$$
$$\phantom{XXXXXXXXXX} CH_2$$
$$\phantom{XXXXXXXXX} d \phantom{X} |$$
$$\phantom{XXXXXXXX} P-(OCH_2-C_7H_{15})_2$$
$$\phantom{XXXXXX} \overset{\diagup}{O} \phantom{XXX} e \phantom{XXX} f$$

Ha + He 3.5——→4.2 ppm (multiplet)
Hc 1.9——→2.4 ppm (multiplet)
Hd + Hb + Hf 0.9——→1.8 ppm (multiplet)

$$(CH_3O)_2P-CH_2-CH-P(OCH_3)_2 \quad (3)$$
$$\phantom{XX}a \phantom{X} \overset{\parallel}{O} \phantom{X} b \phantom{X} | c \phantom{X} \overset{\parallel}{O} \phantom{X} a$$
$$\phantom{XXXXXXXXXX} CH_2$$
$$\phantom{XXXXXXXXX} d \phantom{X} |$$
$$\phantom{XXXXXXXX} P-(OCH_2-C_{11}H_{23})_2$$
$$\phantom{XXXXXX} \overset{\diagup}{O} \phantom{XXX} e \phantom{XXX} f$$

Ha + He 3.5——→4.2 ppm (multiplet)
Hc 1.9——→2.5 ppm (multiplet)
Hb + Hd + Hf 0.6——→1.9 ppm (multiplet)

$$(CH_3O)_2P-CH_2-CH-P(OCH_3)_2 \quad (4)$$
$$\phantom{XX}a \phantom{X} \overset{\parallel}{O} \phantom{X} b \phantom{X} | c \phantom{X} \overset{\parallel}{O} \phantom{X} a$$
$$\phantom{XXXXXXXXXX} CH_2$$
$$\phantom{XXXXXXXXX} d \phantom{X} |$$
$$\phantom{XXXXXXXX} P-(OCH_2-C_{17}H_{35})_2$$
$$\phantom{XXXXXX} \overset{\diagup}{O} \phantom{XXX} e \phantom{XXX} f$$

Ha + He 3.7——→4.4 ppm
Hc 2——→2.4 ppm
Hb + Hd + Hf 0.9——→2 ppm $$(CH_3O)_2-P-CH_2-CH-CH_2-P-(OCH_3)_2 \quad (5)$$
$$\phantom{XX}a \phantom{X} \overset{\parallel}{O} \phantom{X} b \phantom{X} | c \phantom{X} b \phantom{X} \overset{\parallel}{O} \phantom{X} a$$
$$\phantom{XXXXXXXXX} P(OCH_2-C_3H_7)_2$$
$$\phantom{XXXXXX} \overset{\diagup}{O} \phantom{XXX} d \phantom{XXX} e$$

Ha + Hd 3.5——→4.2 ppm (multiplet)
Hb + Hc + He 0.9——→2.5 ppm (multiplet)

$$(CH_3O)_2P-CH_2-CH-CH_2-P(OCH_3)_2 \quad (6)$$
$$\phantom{XX}a \phantom{X} \overset{\parallel}{O} \phantom{X} b \phantom{X} | c \phantom{X} b \phantom{X} \overset{\parallel}{O} \phantom{X} a$$
$$\phantom{XXXXXXXXX} P-(OCH_2-C_7H_{15})_2$$
$$\phantom{XXXXXX} \overset{\diagup}{O} \phantom{XXX} d \phantom{XXX} e$$

Ha + Hb 3.7——→4.2 ppm (multiplet)
Hb + Hc + He 0.9——→2.4 ppm (multiplet)

-continued

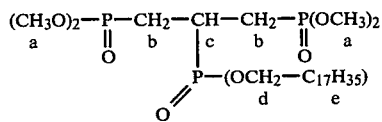

(7)

Ha + Hd 0.9— — →1.6 ppm (multiplet)
Hb + Hc + He 3.6— — →4.0 ppm (multiplet)

$$(CH_3O)_2\underset{a}{-}\underset{\underset{O}{\|}}{P}\underset{b}{-}CH_2\underset{c}{-}\underset{\underset{\underset{O}{\|}}{P}-(OCH_2-C_{17}H_{35})}{CH}\underset{b}{-}CH_2\underset{a}{-}\underset{\underset{O}{\|}}{P}(OCH_3)_2$$ (8)

Ha + Hd 3.5— — →4.2 ppm (multiplet)
Hb + Hc + He 0.7— — →1.8 ppm (multiplet)

EXAMPLES 9 TO 16 (TABLE PAGES 16 AND 17)

Preparation of Triphosphonic Sodium Salts 0.5 mol of one of the triphosphonates prepared in the preceding examples is introduced into a 500 ml round-bottom flask; 0.11 mol of NaI, namely an excess of 10%, and 200 ml of anhydrous acetone are added thereto. The mixture is heated for 4 to 5 hours under reflux. The abundant precipitate which is formed is separated by filtration and washed several times with hot acetone, which leaves lemon-yellow crystals.

The table given below sets forth the melting points, the yields with reference to the diphosphonate used, as well as the characteristic lines of the infrared spectrum for the 8 triphosphonates (9 to 16) prepared.

By controlled acid hydrolysis with hydrochloric acid of the compounds of the following table, the corresponding tetra-ester diacids are obtained.

A more extensive hydrolysis leads to the diester tetra-acids.

EXAMPLE 17

Use for the Extraction of Uranium

The sodium salt of triphosphonate No. 12 (see table, page 16) is tested as extraction agent for a compound of $U^{IV}$ and $Fe^{III}$ from an aqueous solution as compared with the known extraction agent, dioctyl pyrophosphoric acid. The latter, which is considered to be of good efficiency in the art, has the formula

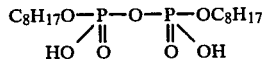

and is designated by the abbreviation OPPA.

The operation consists in treating an aqueous solution of phosphoric acid containing uranyl nitrate which has been previously reduced by iron, with a solution of extractant in kerosene.

The aqueous solution contains, per kilogram, 310 g of $P_2O_5$
200 ppm of uranium in nitrate form
138 ppm of iron in nitrate form.

As to the kerosene, it contains 2.5% chloroform and 3% of the extractant compound to be tested.

To 5 parts by weight of the aqueous solution, there is added 1 part of kerosene solution and the two phases are stirred together for 1 hour at 50° C. After setting aside and decantation, remaining U and Fe are determined in the aqueous solution; by the difference from the above-indicated initial contents there are determined the concentrations of these metals in the kerosene phase.

In the following table the concentrations are expressed per liter based on the density of 0.778 of kerosene and a 1:5 ratio of the two phases present.

| Concentrations in mg/l | OPPA | Triphosphonate No. 12 |
|---|---|---|
| $C_U$ — uranium remaining in the aqueous solution | 39 | 26.5 |
| $C_{Fe}$ — iron remaining in the aqueous solution | 38.5 | 38 |
| $K_U$ — uranium in the kerosene solution | 626 | 675 |
| $K_{Fe}$ — iron in the kerosene solution | 386 | 387 |
| Extraction coefficient $K_U/C_U$ | 16 | 25 |
| Extraction coefficient $K_{Fe}/C_{Fe}$ | 10 | 10 |

It can be seen that product 12 of the invention not only makes it possible to extract more U but it is furthermore more selective with respect to iron; in fact, it extracts more U with respect to iron (coefficients 25:10) than permitted by the OPPA pyrophosphate (coefficients 16:10).

In general, in order to effect the extractions there is added to an aqueous solution, containing the metal to be extracted and 10 to 45% by weight of $H_3PO_4$, 5 to 20% volume of organic liquid (petroleum distillation fraction, such as kerosene, for instance, a $C_8$ to $C_{30}$ alkane, in particular dodecane, and/or a chlorinated $C_1$ to $C_6$ solvent, for instance chloroform, dichlorethane, trichlorethylene, etc.) containing 1 to 30% by weight, and preferably 1 to 10%, of triphosphonic ester or acid in accordance with the invention. Agitation is effected, preferably at a temperature of 30° to 50° C., whereupon the organic layer is separated from the aqueous phase.

| Formula | T F °C. | Yield | νC—H aliphatic | ν(P=O) | ν(P—O—C) |
|---|---|---|---|---|---|
| (9)  | liquid | | | | |

-continued

| Formula | T F °C. | Yield | νC—H aliphatic | ν(P=O) | ν(P—O—C) |
|---|---|---|---|---|---|
| (10) CH₃O\P(=O)(O⁻Na⁺)—CH₂—CH(—CH₂—P(=O)(OC₄H₉)₂)—P(=O)(OCH₃)(O⁻Na⁺) | liquid | | | | |
| (11) CH₃O\P(=O)(O⁻Na⁺)—CH₂—CH(—P(=O)(OC₈H₁₇)₂)—CH₂—P(=O)(OCH₃)(O⁻Na⁺) | >300° C. | 48% | 2860 cm⁻¹ 2950 cm⁻¹ 1470 cm⁻¹ | 1220 cm⁻¹ | 1080 cm⁻¹ |
| (12) CH₃O\P(=O)(O⁻Na⁺)—CH₂—CH(—CH₂—P(=O)(OC₈H₁₇)₂)—P(=O)(OCH₃)(O⁻Na⁺) | >300° C. | 57% | 2950 cm⁻¹ 1475 cm⁻¹ | 1200 cm⁻¹ | 1060 cm⁻¹ |
| (13) CH₃O\P(=O)(O⁻Na⁺)—CH₂—CH(—P(=O)(OC₁₂H₂₅)₂)—CH₂—P(=O)(OCH₃)(O⁻Na⁺) | 226° C. dec | 53% | 2860 cm⁻¹ 2940 cm⁻¹ 1475 cm⁻¹ | 1220 cm⁻¹ | 1070 cm⁻¹ |
| (14) CH₃O\P(=O)(O⁻Na⁺)—CH₂—CH(—CH₂—P(=O)(OC₁₂H₂₅)₂)—P(=O)(OCH₃)(O⁻Na⁺) | 215° C. dec | 71% | 2860 cm⁻¹ 2925 cm⁻¹ 1470 cm⁻¹ | 1210 cm⁻¹ | 1065 cm⁻¹ |
| (15) CH₃O\P(=O)(O⁻Na⁺)—CH₂—CH(—P(=O)(OC₁₈H₃₇)₂)—CH₂—P(=O)(OCH₃)(O⁻Na⁺) | 110° C. | 50% | 2860 cm⁻¹ 2925 cm⁻¹ 1475 cm⁻¹ 725 cm⁻¹ | 1210 cm⁻¹ | 1070 cm⁻¹ |
| (16) CH₃O\P(=O)(O⁻Na⁺)—CH₂—CH(—CH₂—P(=O)(OC₁₈H₃₇)₂)—P(=O)(OCH₃)(O⁻Na⁺) | 208° C. dec | 58% | 2860 cm⁻¹ 2930 cm⁻¹ 1475 cm⁻¹ 725 cm⁻¹ | 1200 cm⁻¹ | 1060 cm⁻¹ |

We claim:

1. A process for the extraction of uranium from an aqueous solution containing 10–45% phosphoric acid thereof which comprises mixing said aqueous solution with a composition comprising an organic liquid containing 1–30% by weight of a triphosphonic ester of the formula

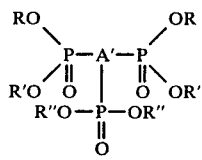

in which A' is a trivalent hydrocarbon grouping having 1 to 6 carbon atoms, R is a C₁ to C₄ alkyl or a hydrogen atom, R' is a C₁ to C₄ alkyl, a hydrogen atom or alkali metal or ammonium cation, and R" is a C₄ to C₁₈ alkyl.

2. Process according to claim 1, wherein the organic liquid selected from the group consisting of petroleum distillates, $C_8$ to $C_{30}$ alkanes and $C_1$ to $C_6$ chlorinated solvents.

3. Process according to claim 2, wherein A' is a $C_3$ aliphatic group.

4. Process according to claim 3 wherein A' is $$-CH_2-CH-CH_2-.$$
$$\phantom{-CH_2-CH}|\phantom{-CH_2-}$$

5. Process according to claim 4, wherein R is methyl, R' is methyl or sodium and R" is selected from the group consisting of $C_4H_9$, $C_8H_{17}$, $C_{12}H_{25}$ and $C_{18}H_{37}$.

6. Process according to claim 5 wherein R' is sodium.

7. Process according to claim 6, wherein said triphosphonic ester is

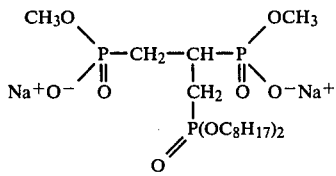

8. A process according to claim 1, wherein the amount of said composition is 5-20% by volume.

* * * * *